United States Patent
Rossi et al.

(10) Patent No.: US 8,299,045 B2
(45) Date of Patent: Oct. 30, 2012

(54) ADENOVIRAL VA1 POL III EXPRESSION SYSTEM FOR RNAI EXPRESSION

(75) Inventors: John J. Rossi, Alta Loma, CA (US); Nan-Sook Lee, Pasadena, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 13/217,518

(22) Filed: Aug. 25, 2011

(65) Prior Publication Data
US 2012/0058522 A1 Mar. 8, 2012

Related U.S. Application Data

(62) Division of application No. 10/629,895, filed on Jul. 30, 2003, now Pat. No. 8,017,759.

(60) Provisional application No. 60/399,397, filed on Jul. 31, 2002.

(51) Int. Cl.
*C12N 15/11* (2006.01)

(52) U.S. Cl. .................................... 514/44 A

(58) Field of Classification Search ................ 514/44 A
See application file for complete search history.

(56) References Cited

U.S. PATENT DOCUMENTS

| | | | |
|---|---|---|---|
| 5,837,503 | A | 11/1998 | Doglio et al. |
| 6,100,087 | A | 8/2000 | Rossi et al. |
| 6,329,201 | B1 | 12/2001 | Polo et al. |
| 6,995,258 | B1 | 2/2006 | Rossi et al. |
| 7,241,618 | B2 | 7/2007 | Agami et al. |
| 2004/0002077 | A1 | 1/2004 | Taira et al. |
| 2004/0005593 | A1 | 1/2004 | Lorens |
| 2005/0048647 | A1 | 3/2005 | Taira et al. |

FOREIGN PATENT DOCUMENTS

| | | |
|---|---|---|
| WO | WO 03/056012 A1 | 7/2003 |
| WO | WO 2004/043406 A2 | 5/2004 |

OTHER PUBLICATIONS

Bertrand, Edouard, et al., "The expression cassette determines the functional activity of ribozymes in mammalian cells by controlling their intracellular localization," *RNA* 3:75-88, 1997.

Brummelkamp, Thijn R., et al., "A System for Stable Expression of Short Interfering RNAs in Mammalian Cells," *Science* 296:550-553, Apr. 19, 2002.

Cagnon, Laurence, et al., "Downregulation of the CCR5 β-Chemokine Receptor and Inhibition of HIV-1 Infection by Stable VA1-Ribozyme Chimeric Transcripts," *Antisense & Nucleic Acid Drug Development* 10:251-261, 2000.

Elbashir, Sayda M., et al., "Duplexes of 21-nucleotide RNAs mediate RNA interference in cultured mammalian cells," *Nature* 411:494-498, May 24, 2001.

Good, P.D., et al., "Expression of small, therapeutic RNAs in human cell nuclei," *Gene Therapy* 4:45-54, 1997.

Paul, Cynthia P., et al., "Effective expression of small interfering RNA in human cells," *Nature Biotechnology* 20:505-508, May 2002.

Yu, Jenn-Yah, et al., "RNA interference by expression of short-interfering RNAs and hairpin RNAs in mammalian cells," *PNAS* 99(9):6047-6052, Apr. 2002.

Sharp, Phillip A., et al., "RNA interference—2001," *Genes & Development* 15:485-490, 2001.

Lau et al., Science, 294: 858-862, 2001.

Frey et al., Abstracts of General Meeting of the American Society for Microbiology 1992, 92, 225, H-254.

Ambros, Cell, 2001, 107:823-6.

Billy et al., *PNAS*, 98: 14428-14433, 2001.

Bernstein et al., Nature, 2001, 409: 363-6.

Zeng et al., Mol. Cell, 9, 1327-33, 2002.

Cordelier, Pierre, et al., "Targeting CCR5 with siRNAs: Using Recombinant SV40-Derived Vectors to Protect Macrophages and Microglia from R5-Tropic HIV," *Oligonucleotides* 13:281-294 (2003).

Li, Ming-Jie, et al., "Inhibition of HIV-1 Infection by Lentiviral Vectors Expressing Pol III-Promoted Anti-HIV RNAs," *Molecular Therapy*, vol. 8, No. 2, pp. 196-206, Aug. 2003.

Paddison et al., Genes Dev., 16: 948-958, 2002.

Maria Fe C Medina, et al., "RNA polymerase III-driven expression cassettes in human gene therapy," Molecular Therapeutics, 1999, vol. 1, No. 5, pp. 580-594.

Nan Sook Lee, et al., "Expression of small interfering RNAs targeted against HIV-1 *rev* transcripts in human cells," Nature Biotechnology, May 2002, vol. 19, pp. 500-505.

Shen, Hong Ming et al., "The 3' Igk enhancer contains RNA polymerase II promoters: implications for endogenous and transgenic κ gene expression," International Immunology, vol. 13, No. 5, pp. 665-674, © 2001 The Japanese Society for Immunology.

*Primary Examiner* — Brian Whiteman
(74) *Attorney, Agent, or Firm* — Rothwell, Figg, Ernst & Manbeck p.c.

(57) ABSTRACT

An adenoviral VA1 Pol III expression system for RNAi expression is provided.

12 Claims, 5 Drawing Sheets

ADENOVIRAL VA1 POL III EXPRESSION SYSTEM FOR RNAI EXPRESSION

CROSS-REFERENCE TO RELATED APPLICATIONS

This application is a division of U.S. patent application Ser. No. 10/629,895 filed on 30 Jul. 2003 (now U.S. Pat. No. 8,017,759), which in turn is related to and claims priority under 35 U.S.C. §119(e) to U.S. Provisional Application Ser. No. 60/399,397, filed 31 Jul. 2002. Each application is incorporated herein by reference in its entirety.

STATEMENT OF FEDERALLY SPONSORED RESEARCH

This invention was made with federal government support from the National Institutes of Health of the U.S. Department of Health and Human Services under Grant No. A129329 to the City of Hope. The United States government has certain rights in the invention.

SEQUENCE SUBMISSION

The present application is being filed along with a Sequence Listing in electronic format. The Sequence Listing is entitled 1954556SequenceListing.txt, was created on 24 Aug. 2011 and is 2 kb in size. The information in the electronic format of the Sequence Listing is incorporated herein by reference in its entirety.

FIELD OF THE INVENTION

The present invention relates to RNA interference (RNAi), and more particularly to expression systems for producing interfering RNA molecules, including small interfering RNA molecules (siRNAs) and siRNA precursors in mammalian cells.

BACKGROUND OF THE INVENTION

Gene therapy remains a promising treatment for AIDS because of the limited effectiveness of existing antiviral agents such as immunotherapy, protease inhibitors and vaccines. Several types of RNA gene therapies have been developed and shown to inhibit HIV-1 replication in mammalian cell cultures; these include antisense RNA, catalytic RNA (ribozymes) and high-affinity RNA ligands (apamers or decoys). However, their efficiencies appear to be highly variable and, in many cases, ineffective.

RNA interference (RNAi) is the process of sequence-specific, post-transcriptional gene silencing in animals and plants initiated by double-stranded RNA that is homologous in sequence to the silenced gene. (Sharp, P. A., 2001) This powerful genetic technology has recently been shown to be useful in mammalian cells (Elbashir, S. M., et al., 2001; Novina, C. D., et al., 2002; Brummelkamp, T. R., et al., 2002; Paddison, P. I., et al., 2002; Lee, N. S., et al., 2002). One form of double-stranded RNA, known as small interfering RNA (siRNA), has been shown to target and inhibit expression of HIV-1 genes. (Lee, N. S., et al., 2002)

It is known that dsRNA≧30 bp can trigger interferon responses in mammalian cells that are intrinsically sequence-nonspecific to the inducing dsRNA. (Elabashir, S. M., et al., 2001) Duplexes of 21-nucleotides (siRNAs) with overhanging 3' ends can mediate RNAi in a sequence-specific manner in cultured mammalian cells. (Elbashir, S. M., et al., 2001)

In mammalian systems, the sequence-specific RNAi effect can be observed by introducing siRNAs into target cells directly by transfection (Elbashir, S. M., et al., 2001 and Novina, C. D., et al., 2002), or indirectly by endogenous expression of siRNAs or short hairpin siRNAs (shRNAs). (Brummelkamp, T. R., et al., 2002; Paddison, P. I., et al., 2002; and Lee, N. S., et al., 2002). The stem-loop parts of the shRNAs parallel the naturally occurring stem-loop structures that are processed by the Dicer to yield small temporal RNAs (stRNAs) or microRNAs (miRNAs). Therefore, expression of shRNAs or miRNA precursors corresponding to HIV-1 sequences could be acted upon by the human Dicer to yield HIV-specific siRNAs. Recently, expression of several shRNAs having different stem-loop structures from DNA templates in mammalian cells silenced several targets as effectively as synthetic siRNAs. (Brummelkamp, T. R., et al., 2002; and Paddison, P. I., et al., 2002) However, it remains unclear what makes the best RNA silencing hairpin.

Inhibition of HIV-1 replication using synthetic siRNAs or siRNAs expressed from plasmid DNAs has shown that siRNA technology may be useful as a therapeutic strategy to inhibit HIV-1 replication and infection in host cells. (Novina, C. D., et al., 2002; Paddison, P. I., et al., 2002; and Jacque, J.-M., et al. 2002) These data provide a basis for investigating therapeutic uses of siRNAS as anti-HIV-1 agents. For this purpose, siRNAs are expressed in cells to confer immunity to HIV-1 infection and prevent viral replication.

One approach for expressing siRNAs in cells involves inserting siRNA genes into a viral vector to be transduced into primary cells. Vector-based strategies that target combinations of viral genes and/or cellular genes should provide an improvement to RNA-based antiviral therapeutics. CCR5, an HIV-1 co-receptor, provides an attractive target candidate because homozygous deletions in CCR5 effectively confer protection from HIV-1 without any serious deleterious effects in immune functions in humans. A vector-based strategy for silencing HIV-1 rev in human cells has been demonstrated using the U6 promoter system. (Paddison, P. I., et al., 2002).

The basic design of the VA1 vector is described in Cagnon and Rossi, *Antisense and Nucleic Acid Drug Development* 10:251-261, 2000, incorporated herein by reference. The use of the adenoviral VA1 promoter for ribozyme expression is described in U.S. Pat. No. 6,100,087 (Rossi et al.), which also is incorporated herein by reference.

Vector-based siRNA-directed gene silencing in primary cells is lower than that seen in cell lines possibly because of poor expression of siRNAs or lower efficiency of silencing machinery in primary cells.

Strategies are needed to improve the expression and efficacy of silencing RNAs in primary cells. Strategies include alternative promoter systems for expressing interfering RNA molecules, and particularly siRNAs, in primary cells. The present invention addresses this need.

SUMMARY OF THE INVENTION

In one aspect, the present invention provides a VA1 Pol III promoter system, and preferably an adenoviral VA1 promoter system, for expressing interfering RNA (RNAi) molecules, including siRNA and siRNA precursor molecules, in a cell, preferably a mammalian cell. One advantage of this promoter system is that the VA1 transcript is transported to the cytoplasm, which is where the RNAi associated enzyme Dicer is localized.

In a preferred embodiment, a construct encoding an RNAi molecule is embedded in a non-essential stem region of the VA1 promoter gene. The RNAi molecule is expressed as a double stranded RNA, which may include a shRNA or other siRNA precursor that can serve as a substrate for the enzyme Dicer, which digests the RNA into an about 21-23 nucleotide duplex that can function as an siRNA.

In another preferred embodiment, the VA1 gene contains a construct encoding a precursor microRNA (miRNA), which may provide higher expression levels or efficacy in primary cells. miRNA precursors likely are processed by the enzyme dicer into an about 21-24 nucleotide siRNA. In a more preferred embodiment, human mir-30 and let-7a-3 miRNAs may be utilized because of their RNAi effect in human cells.

In another aspect, the present invention provides methods for expressing RNAi molecules in mammalian cells using the above-described adenoviral VA1 Pol III promoter system. The methods are useful for inhibiting gene expression and/or replication.

In a further aspect, the invention provides a mammalian cell, preferably a primary cell, into which has been introduced a VA1 promoter system containing a construct encoding an interfering RNA molecule. The construct and VA1 promoter gene preferably are operatively linked.

BRIEF DESCRIPTION OF THE DRAWINGS

FIG. 2A shows that miRNA encoding sequences are inserted at the BstEII site of the VA1 gene. The pol III promoter is represented by the A and B boxes.

FIG. 2B shows two preferred human miRNA constructs (gugaagccacagaug (SEQ ID NO: 2), uggggcucug cccugcuaug ggau (SEQ ID NO: 3).

FIG. 2C shows expressed VA1 RNA (from Mfold version 3.0) containing miRNA.

DETAILED DESCRIPTION OF THE INVENTION

In the present invention, an RNA polymerase III (Pol III)-based adenoviral VA1 promoter gene (e.g., FIG. 1A) is used to control expression of interfering RNAs, including siRNAs and siRNA precursors, in mammalian cells and preferably primary cells.

The VA1 Pol III promoter is able to tolerate variability in the sequences separating the two promoter control elements. Silencing RNA encoding sequences can be inserted within the coding region, preferably stem-loop IV, of the VA1 gene, enabling silencing RNAs to be efficiently transcribed and stabilized by the secondary and tertiary structures of the natural RNA. VA1 transcripts are also primarily located in the cytoplasm where essential siRNA machinery such as silencing complexes (RISC) and Dicer are located. The cytoplasmic co-localization of the VA1 RNA with the siRNA machinery may improve the efficiency of siRNA-mediated RNAi.

Figure 2:
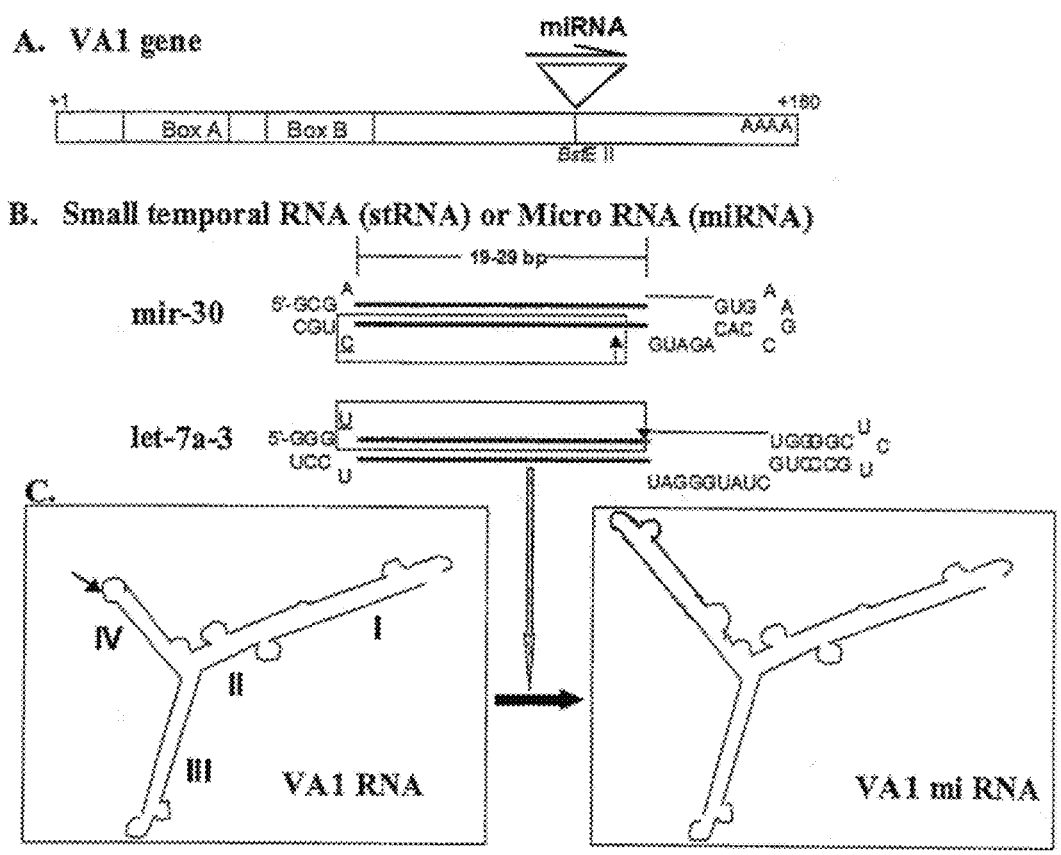
FIGS. 2A-C are schematic diagrams of a VA1 expression cassette, precursor siRNA constructs, and VA1 promoter-siRNA precursor expression products.

In a preferred embodiment, miRNA precursors are appropriate silencing RNAs for cloning into VA1 RNA because they are likely processed by Dicer into about 21-24 nucleotide siRNAs (FIG. 2B). Among the many human miRNAs, natural and designed mir-30 miRNAs can inhibit the expression of target mRNAs in human cells. (Zeng, Y., et al. 2002). Human mir-30 and let-7a-3 miRNAs (having similar structure to mir-30) are useful for this purpose because of their RNAi effect in human cells. The constructs encoding miRNA precursors, containing the duplex sequences of the rev or CCR5 mRNA, can be designed and produced by PCR using DNA forward and reverse oligomers.

Before cloning into the VA1 vector, the designed mir-30 or let7 rev or CCR5 miRNA precursor constructs can be transcribed in vitro using DNA oligomer templates and T7 megashortscript kit (Ambion) to test their susceptibility to Dicer. Transcription templates are designed that contain T7 promoter sequences at the 5' end. The T7 transcribed miRNAs then are incubated with human Dicer and the products are visualized in a PAGE gel.

To determine whether Dicer is involved in RNAi in vivo, Dicer activity can be depleted from the transfected cells with Dicer siRNAs.

In a preferred embodiment, the miRNAs that are siRNA targeted against rev and/or CCR5 mRNA are cloned into the VA1 vectors using BstEII sites (FIG. 2A). The constructs as well as control constructs are co-transfected into 293/EcR cells with the pIND-rev-EGFP or pIND-CCR5-EGFP target constructs. Inhibitory efficacy is monitored using assays, including FACS and fluorescent microscope imaging.

The intracellular localization of miRNA-VA1 constructs can be examined using in situ hybridization. (Lee, N. S., et al., 1999) A modified, Cy3-labeled DNA probe complementary to the insert in the VA1 cassette and a FITC-labeled DNA probe complementary to the target can be used for this purpose. Appropriate controls complementary to intracellular sequences (U3 for the nucleolus, U6 for the nucleus, and tRNA lys for the cytoplasm) also can be used along with a third fluorochrome to confirm the intracellular compartment. Following preliminary identification of effective shRNA constructs, they are expressed in human CD34+ cells and T-cells challenged with HIV-1.

Resistance to siRNAs can and will occur in HIV-1 infected individuals. To circumvent this problem, vectors can be produced that simultaneously express multiple siRNAs targeted to different sites in the virus, preferably along with an siRNA targeted against the cellular co-receptor CCR5.

Before gene therapy, the anti-HIV-1 candidate constructs are effectively transduced into primary cells or quiescent stem cells. Candidate constructs can be subcloned into a vector, examples of which are described in co-pending U.S. application Ser. No. 10/365,643, now U.S. Pat. No. 7,820,632, filed Feb. 13, 2003, incorporated herein by reference.

Candidate constructs are subcloned preferably into a lentiviral vector, and more preferably an HIV7 lentiviral vector. The HIV7 lentiviral vector contains the polypurine tract of HIV-1 for enhanced integration and the woodchuck hepatitis post-transcriptional regulatory element (WCRE) for enhancing RNA stability. The 5' LTR is replaced in the vectors with the CMV promoter that subsequently is eliminated on reverse transcription of the viral RNA. In the final construct, the Pol III cassette is inserted downstream of the polypurine tract and Rev response element (RRE) and immediately upstream of the CMV promoter in pHIV-7. The EGFP gene also can be inserted into the vector to provide a selection marker.

In a preferred embodiment, the vectors harboring VA1 miRNAs are packaged by co-transfecting them along with pCMV-G expressing the VSV G protein, pCHGP-2 expressing the HIV-1 Gag and Pol proteins, and pCMV-Rev. CEM cells are used to pre-screen the expression levels of the constructs prior to their expression in primary cells. Using supernatants from transfected 293T cells, the CEM cells are transduced and the expression levels of lentiviral vectors harboring VA1 miRNAs are analyzed using Northern gel analyses.

The transductants then are infected with lab strains of HIV-1 such as M-tropic JRFL and BaL and T-tropic IIIB and NL4-3. Suppression of viral replication is determined by monitoring RT and p24 levels, syncytia formation, and survivability. Once the constructs are determined to function properly, they are then transduced into primary CD34+ cells and T-lymphocytes using, for example, the protocol by Bauer et al. (Bauer, G. et al., 1997) Transduced cells then are evaluated for siRNA expression and anti-HIV-1 activities.

The present invention is further detailed in the following Examples, which are attached by way of illustration and are not intended to limit the invention in any manner.

EXAMPLE 1

Figure 1A:
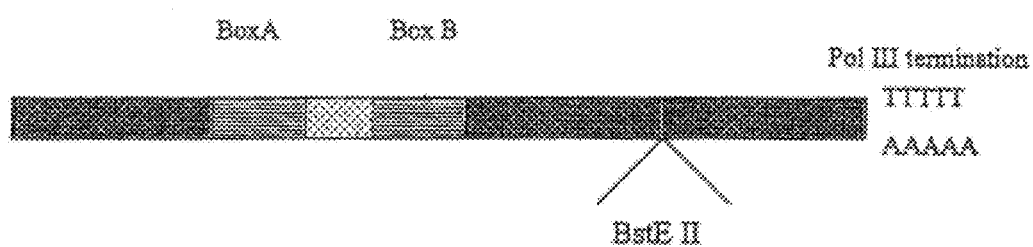
FIG. 1A is a schematic diagram of an RNA Pol III-based adenoviral VA1 expression construct in accordance with the invention. The diagram depicts the VA1 gene and insertion site for an siRNA or siRNA precursor construct.
Figure 1B:
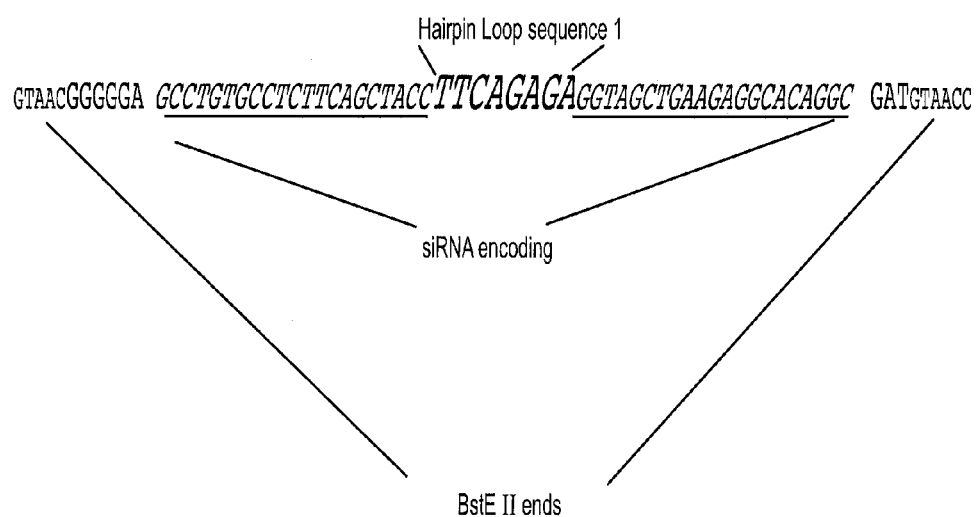
FIG. 1B (SEQ ID NO: 1) depicts an siRNA hairpin precursor (shRNA) targeted to an HIV rev site II, which can be inserted at the BstEII site of a VA1 gene.

VA1-miRNAs and VA1-siRNAs can contain 1) 21-nt sense, 2) 4, 8, or 9 base loop for siRNA or miRNA (mir-30 or let-7a-3), and 3) 21-nt antisense strand complementary to a HIV-1 rev target (total ~50-nt). To make inactive mutant mi- or si-RNA variants, 4-nt in the middle of the stem sequences were mutated to be non-complementary to the target. BstEII restriction fragments containing mi- or si-RNA sequences are prepared from synthetic oligonucleotides, which share 12 bases of complementary sequence at their 3' end. These were annealed and the primer ends extended using Taq polymerase and several rounds of PCR. The wt and mt mi- or si-RNA sequences are cloned into the BstEII site of pVA1 (FIG. 1A). The sequences of the loops are: 4 base loop: TTAA (SEQ ID NO: 4), 8 base loop: GAAGCTTG (SEQ ID NO: 5) (underlined: HindIII site), and 9 base loop: TTCAAGAGA (SEQ ID NO: 6). As shown in FIG. 1B, the DNA sequence (SEQ ID NO:7) encoding a short hairpin RNA cloned into the BstEII site of pVA1 comprises a 21 nt sense strand, a 8 nt hairpin loop and a 21 nt antisense strand complementary to a HIV-1 rev target. The 8 nt hairpin loop shown in FIG. 1B is SEQ ID NO:8.

EXAMPLE 2

Figure 3:
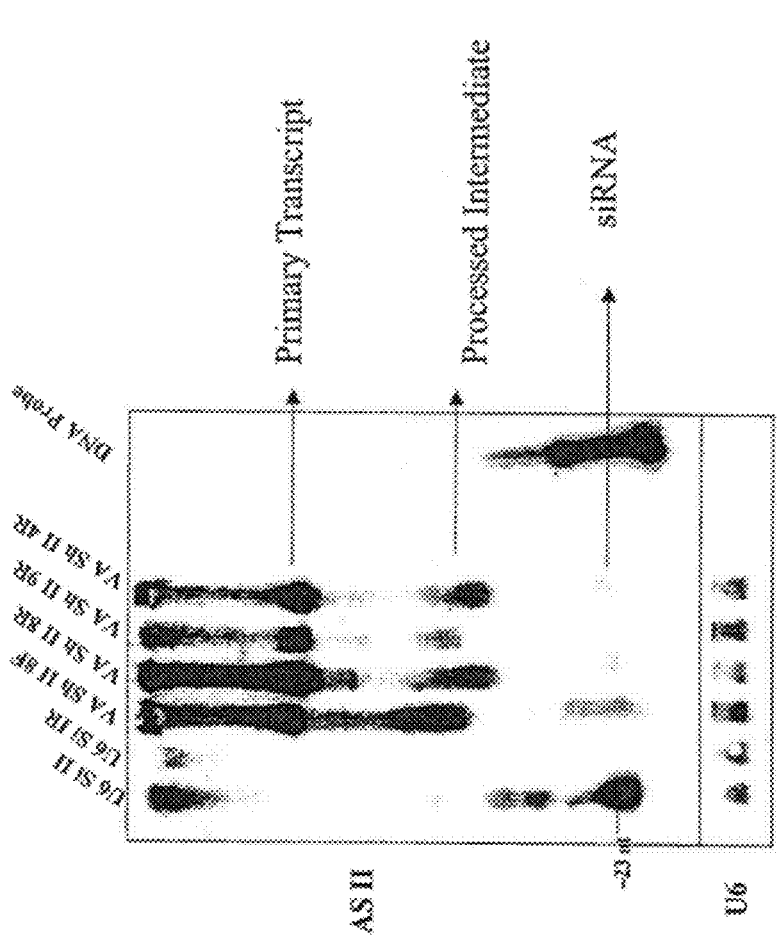
FIG. 3 is a photograph of results of Northern gel analyses of expression of VA1-siRNA constructs in accordance with the invention. The lanes are left to right: U6 siII, U6si-irrelevant, VAsh-siteII with 8 base loop, VAsh-site II inverted (antisense-loop-sense) with 8 base loop, VAshII inverted with 9 base loop, VAshII inverted with 4 base loop, DNA oligo size marker. The 23 nucleotide transcript from the U6 promoter siRNAII is indicated. Full length, intermediate processed and siRNA processed products also are depicted.

VA1-siRNA expression constructs targeting rev site II were co-transfected with a rev-EGFP fusion construct. (FIG. 3) The various VA1 shRNA chimeric constructs or a U6 promoter siRNA expression construct were transfected using a cationic lipid into human 293 cells. Forty eight hours after transfection, RNAs were isolated from the cells and electrophoresed in a 6% denaturing polyacrylamide gel. The RNAs were electroblotted to a nylon membrane and hybridized with a $^{32}$P-labeled synthetic DNA oligonucleotide complementary to the antisense sequence of the shRNA or siRNA.

EXAMPLE 3

Figure 4:
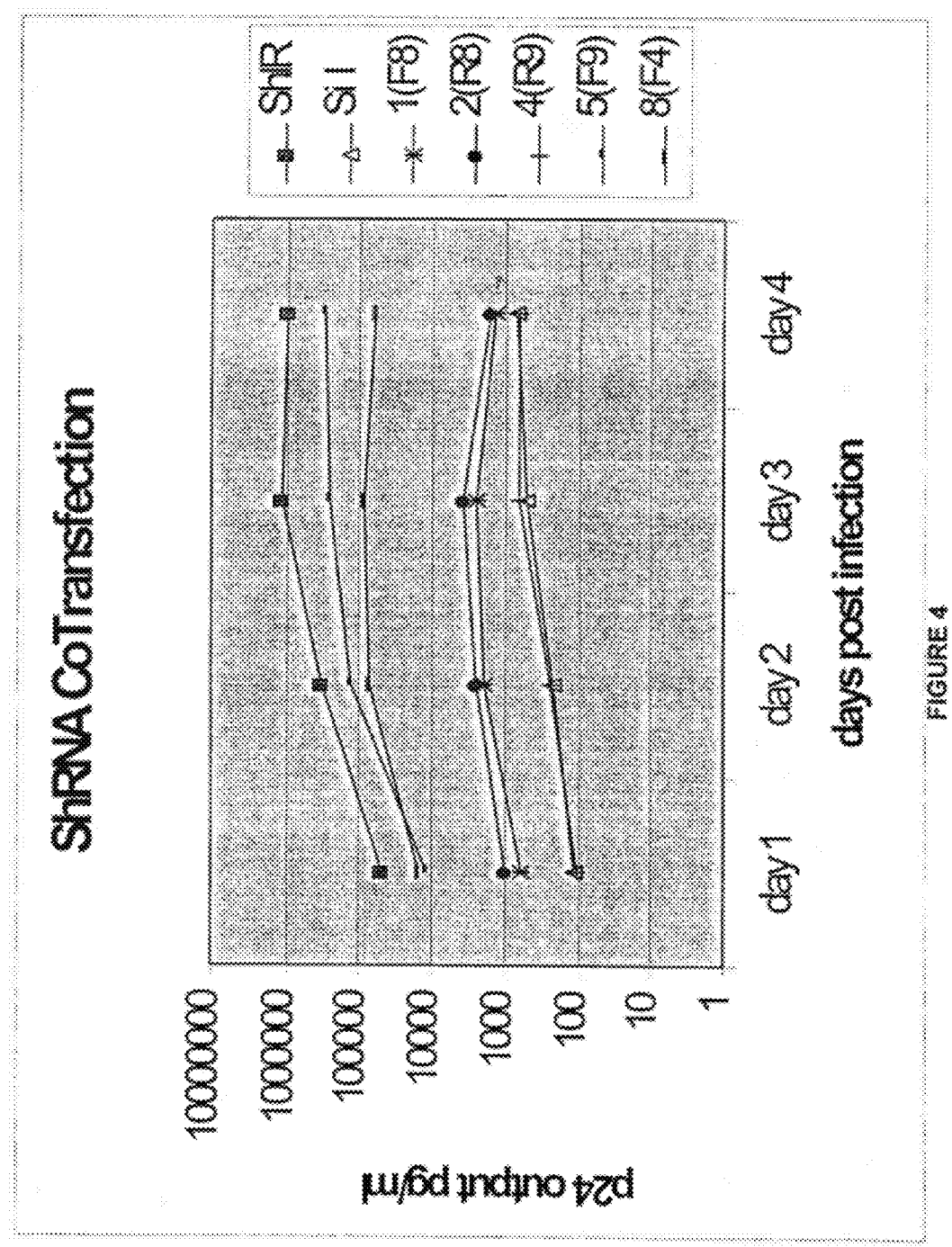
FIG. 4 is a graph showing the results of co-transfecting chimeric VA1 shRNA constructs with HIV-1 pNL4-3 proviral DNA into human 293 cells. The various VA1-shRNA chimeric constructs are indicated along with the positive control U6 siRNA expression construct. The letters F and R refer to the orientation of the shRNA sequence in the VA1 vector with respect to the transcription start point. F=forward sense-loop-antisense and R=reverse antisense-loop-sense. The loop sizes are also indicated.

Several different loop sizes and the relative orientations of the sense and antisense strands were tested by co-transfecting VA1-siRNA constructs with pNL4-3 in human 293 cells. Plasmids encoding the various constructs were co-transfected with HIV-1 proviral DNA into human 293 cells and HIV-1 p24 assays were carried out on samples taken at the times indicated. The results (FIG. 4) demonstrate that an 8 base loop was among the most effective at generating a functional siRNA, and that the relative orientation of sense and antisense (#1 and #2) do not appear to affect the efficacy of the siRNAs.

The publications and other materials used herein to illuminate the background of the invention, and provide additional details respecting the practice of the invention, are incorporated herein by reference as if each was individually incorporated herein by reference.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LISTED REFERENCES

Bauer, G. et al., *Blood* 89:2259-2267, 1997.
Brummelkamp, T. R., et al., *Science* 296:550-553, 2002.
Elbashir, S. M., et al., *Nature* 411:494-498, 2001.
Jacque, J.-M., et al. *Nature* 418: 435-438, 2002.
Lee, N. S., et al., *RNA* 5:1200-1209, 1999.
Lee, N. S., et al., *Nature Biotechnol.* 119:500-505, 2002.
Novina, C. D., et al., *Nature Med.* 8:681-686, 2002.
Paddison, P. I., et al., *Genes Dev.* 16:948-958, 2002.
Sharp, P. A. *Genes Dev.* 15:485-490, 2001.
Zeng, Y., et al. *Mol. Cell* 9:1327-1333, 2002.

We claim:

1. A method for expressing an interfering RNA molecule in a mammalian cell, comprising:
   (a) introducing into a mammalian cell an expression cassette comprising an adenoviral VA1 gene and a nucleic acid encoding an interfering RNA (RNAi) precursor molecule, wherein the adenoviral VA1 gene comprises the adenoviral VA1 promoter and a coding sequence for the VA1 RNA, wherein the nucleic acid is inserted at a BstEII site within a non-essential stem region of the adenoviral VA1 coding sequence, wherein the nucleic acid encoding the RNAi precursor molecule encodes a hairpin siRNA (shRNA) or a precursor microRNA (precursor miRNA);
   (b) maintaining the mammalian cell produced in step (a) under conditions and for a time sufficient to express the VA1 RNA containing the RNAi precursor molecule and to cleave the RNAi precursor molecule out of the VA1 RNA; and
   (c) maintaining the mammalian cell produced in step (b) under conditions and for a time sufficient for Dicer to cleave the RNAi precursor molecule to produce an interfering RNA molecule, wherein the RNA interfering molecule is an siRNA or a miRNA.

2. The method of claim 1, wherein the RNAi precursor molecule encoding nucleic acid encodes a hairpin siRNA (shRNA).

3. The method of claim 1, wherein the RNAi precursor molecule encoding nucleic acid encodes a precursor miRNA.

4. The method of claim 1, wherein the RNAi precursor molecule encoding nucleic acid is SEQ ID NO:7.

5. The method of claim 1, wherein the RNAi precursor molecule encoding nucleic acid is SEQ ID NO:2.

6. The method of claim 1, wherein the RNAi precursor molecule encoding nucleic acid is SEQ ID NO:3.

7. A method for producing a double stranded RNA precursor molecule in a mammalian cell, comprising:
   (a) introducing a vector into a mammalian cell, wherein the vector comprises an expression cassette comprising an adenoviral VA1 gene and a nucleic acid encoding an interfering RNA (RNAi) precursor molecule, wherein the adenoviral VA1 gene comprises the adenoviral VA1 promoter and a coding sequence for the VA1 RNA, wherein the nucleic acid is inserted at a BstEII site within a non-essential stem region of the adenoviral VA1 coding sequence, wherein the nucleic acid encoding the RNAi precursor molecule encodes a hairpin siRNA (shRNA) or a precursor microRNA (precursor miRNA);
   (b) maintaining the mammalian cell produced in step (a) under conditions and for a time sufficient to express the VA1 RNA containing the RNAi precursor molecule, wherein the RNAi precursor molecule is inactive in the VA1 RNA; and
   (c) maintaining the mammalian cell produced in step (b) under conditions and for a time sufficient to cleave the RNAi precursor molecule out of the VA1 RNA, wherein the cleaved RNAi precursor molecule is a double stranded RNA molecule and is a substrate for Dicer.

8. The method of claim 7, wherein the RNAi precursor molecule encoding nucleic acid encodes a hairpin siRNA (shRNA).

9. The method of claim 7, wherein the RNAi precursor molecule encoding nucleic acid encodes a precursor miRNA.

10. The method of claim 7, wherein the RNAi precursor molecule encoding nucleic acid is SEQ ID NO:7.

11. The method of claim 7, wherein the RNAi precursor molecule encoding nucleic acid is SEQ ID NO:2.

12. The method of claim 7, wherein the RNAi precursor molecule encoding nucleic acid is SEQ ID NO:3.

* * * * *

SEQUENCE LISTING

<160> NUMBER OF SEQ ID NOS: 8

<210> SEQ ID NO 1
<211> LENGTH: 70
<212> TYPE: DNA
<213> ORGANISM: Artificial Sequence
<220> FEATURE:
<223> OTHER INFORMATION: siRNA expression construct
<220> FEATURE:

```
<221> NAME/KEY: misc_feature
<222> LOCATION: (1)..(11)
<223> OTHER INFORMATION: BstII end
<220> FEATURE:
<221> NAME/KEY: misc_feature
<222> LOCATION: (12)..(61)
<223> OTHER INFORMATION: siRNA encoding region
<220> FEATURE:
<221> NAME/KEY: misc_feature
<222> LOCATION: (33)..(40)
<223> OTHER INFORMATION: hairpin loop sequence
<220> FEATURE:
<221> NAME/KEY: misc_feature
<222> LOCATION: (52)..(70)
<223> OTHER INFORMATION: BstII end

<400> SEQUENCE: 1
gtaacggggg agcctgtgcc tcttcagcta ccttcagaga ggtagctgaa gaggcacagg    60
cgatgtaacc                                                          70

<210> SEQ ID NO 2
<211> LENGTH: 15
<212> TYPE: RNA
<213> ORGANISM: Artificial Sequence
<220> FEATURE:
<223> OTHER INFORMATION: partial miRNA construct

<400> SEQUENCE: 2
gugaagccac agaug                                                    15

<210> SEQ ID NO 3
<211> LENGTH: 24
<212> TYPE: RNA
<213> ORGANISM: Artificial Sequence
<220> FEATURE:
<223> OTHER INFORMATION: partial miRNA construct

<400> SEQUENCE: 3 ugggggcucug cccugcuaug ggau                                         24

<210> SEQ ID NO 4
<211> LENGTH: 4
<212> TYPE: DNA
<213> ORGANISM: Artificial Sequence
<220> FEATURE:
<223> OTHER INFORMATION: loop

<400> SEQUENCE: 4 ttaa                                                                 4

<210> SEQ ID NO 5
<211> LENGTH: 8
<212> TYPE: DNA
<213> ORGANISM: Artificial Sequence
<220> FEATURE:
<223> OTHER INFORMATION: loop

<400> SEQUENCE: 5 gaagcttg                                                             8

<210> SEQ ID NO 6
<211> LENGTH: 9
<212> TYPE: DNA
<213> ORGANISM: Artificial Sequence
<220> FEATURE:
<223> OTHER INFORMATION: loop

<400> SEQUENCE: 6
```

```
-continued ttcaagaga                                                        9

<210> SEQ ID NO 7
<211> LENGTH: 50
<212> TYPE: DNA
<213> ORGANISM: Artificial Sequence
<220> FEATURE:
<223> OTHER INFORMATION: siRNA encoding short hairpin oligonucleotide
<220> FEATURE:
<221> NAME/KEY: misc_feature
<222> LOCATION: (1)..(21)
<223> OTHER INFORMATION: DNA encoding sense strand of siRNA for HIV rev
      target
<220> FEATURE:
<221> NAME/KEY: misc_feature
<222> LOCATION: (22)..(29)
<223> OTHER INFORMATION: DNA encoding RNA hairpin loop
<220> FEATURE:
<221> NAME/KEY: misc_feature
<222> LOCATION: (30)..(50)
<223> OTHER INFORMATION: DNA encoding antisense strand of siRNA
      complementary to a HIV-1 rev target

<400> SEQUENCE: 7
gcctgtgcct cttcagctac cttcagagag gtagctgaag aggcacaggc          50

<210> SEQ ID NO 8
<211> LENGTH: 8
<212> TYPE: DNA
<213> ORGANISM: Artificial Sequence
<220> FEATURE:
<223> OTHER INFORMATION: hairpin loop

<400> SEQUENCE: 8 ttcagaga                                                         8
```